United States Patent
Knowlson et al.

(10) Patent No.: US 11,879,212 B2
(45) Date of Patent: Jan. 23, 2024

(54) PLASTIC FREE WET WIPES WITH HIGH BULK AND WET STRENGTH

(71) Applicants: Richard Paul Knowlson, Charlotte, NC (US); Matthew Lee Koele, Random Lake, WI (US); Matthew Russell Roberts, Lowell, AR (US); Fernando Romo Lopez, Cave Springs, AR (US)

(72) Inventors: Richard Paul Knowlson, Charlotte, NC (US); Matthew Lee Koele, Random Lake, WI (US); Matthew Russell Roberts, Lowell, AR (US); Fernando Romo Lopez, Cave Springs, AR (US)

(73) Assignee: Rockline Industries Inc., Sheboygan, WI (US)

( * ) Notice: Subject to any disclaimer, the term of this patent is extended or adjusted under 35 U.S.C. 154(b) by 87 days.

(21) Appl. No.: 17/212,675

(22) Filed: Mar. 25, 2021

(65) Prior Publication Data

US 2021/0301467 A1    Sep. 30, 2021

Related U.S. Application Data

(60) Provisional application No. 62/994,586, filed on Mar. 25, 2020.

(51) Int. Cl.
*D21H 11/00*    (2006.01)
*D21H 15/04*    (2006.01)
(Continued)

(52) U.S. Cl.
CPC .............. *D21H 11/00* (2013.01); *D04H 1/587* (2013.01); *D04H 1/732* (2013.01); *D21H 15/04* (2013.01); *D04H 1/64* (2013.01)

(58) Field of Classification Search
CPC ........ D21H 11/00; D21H 15/04; D21H 21/22; D21H 21/18; D04H 1/425; D04H 1/58;
(Continued)

(56) References Cited

U.S. PATENT DOCUMENTS 5,281,306 A  *  1/1994  Kakiuchi ............. C11D 17/041
                                                    162/158
7,585,797 B2 *  9/2009  Vogel ....................... D04H 1/64
                                                    442/361
(Continued)

FOREIGN PATENT DOCUMENTS

WO    WO 2015/047987 A1    4/2015
WO    WO 2018/184048 A1    10/2018
WO    WO-2021195408 A1 *  9/2021  ........... A61K 8/0208

*Primary Examiner* — Jose A Fortuna
(74) *Attorney, Agent, or Firm* — Reinhart Boerner Van Deuren P.C.

(57) ABSTRACT

A wet wipe is provided. The wet wipe includes a sheet formed from non-plastic materials. The sheet has a weight of between 40-90 gsm. The sheet comprises a blend of wood pulp fluff fiber and cellulosic staple fibers and/or cross-linked curly pulp. The wood pulp fluff fiber has a weight percent of between 60-95%. The cellulosic staple fibers and/or cross-linked curly pulp has a weight percent of between 40-5%. A plastic free binder is included. The sheet has an effective wet strength of at least 150 grams per linear inch in the cross-direction.

26 Claims, 6 Drawing Sheets

(51) Int. Cl.
  *D04H 1/732* (2012.01)
  *D04H 1/587* (2012.01)
  *D04H 1/64* (2012.01)

(58) Field of Classification Search
  CPC .......... D04H 1/587; D04H 1/64; D04H 1/732; A61K 2800/10; A61K 8/0208; A61K 8/027; A61Q 19/00
  See application file for complete search history.

(56) References Cited

U.S. PATENT DOCUMENTS

| | | | | |
|---|---|---|---|---|
| 8,501,647 | B2* | 8/2013 | Hurley | D04H 1/5418 428/296.7 |
| 8,871,053 | B2* | 10/2014 | Sealey | D21H 21/14 428/920 |
| 9,439,549 | B2* | 9/2016 | Dutkiewicz | D21H 27/38 |
| 9,863,073 | B2* | 1/2018 | Stralin | D04H 1/43838 |
| 10,405,724 | B2* | 9/2019 | Baker | A47L 13/16 |
| 10,973,384 | B2* | 4/2021 | Baker | D04H 1/587 |
| 11,326,283 | B2* | 5/2022 | Carlyle | D04H 3/013 |
| 2001/0023160 | A1* | 9/2001 | Yamada | D04H 1/64 442/413 |
| 2003/0100240 | A1 | 5/2003 | Takai et al. | |
| 2003/0113463 | A1 | 6/2003 | Ko et al. | |
| 2004/0103970 | A1* | 6/2004 | Quederni | D04H 1/4291 442/361 |
| 2006/0008621 | A1* | 1/2006 | Gusky | D04H 1/00 428/156 |
| 2011/0293931 | A1* | 12/2011 | Vogel | A61Q 19/10 428/221 |
| 2012/0144611 | A1* | 6/2012 | Baker | D04H 1/44 15/104.93 |
| 2014/0173841 | A1* | 6/2014 | Hurley | A61K 8/365 15/104.93 |
| 2015/0135457 | A1* | 5/2015 | Dutkiewicz | D04H 1/44 15/209.1 |
| 2015/0238062 | A1* | 8/2015 | Baker | D04H 1/70 15/223 |
| 2016/0183758 | A1* | 6/2016 | Baker | D04H 1/44 162/132 |
| 2017/0254025 | A1 | 9/2017 | Miller et al. | |
| 2017/0303762 | A1* | 10/2017 | Baker | A47L 13/16 |
| 2018/0344120 | A1* | 12/2018 | Baker | D04H 1/425 |
| 2019/0365189 | A1* | 12/2019 | Baker | D21H 27/38 |
| 2021/0301467 | A1* | 9/2021 | Knowlson | D21H 15/04 |
| 2022/0002921 | A1* | 1/2022 | Salam | D04H 1/593 |
| 2022/0388269 | A1* | 12/2022 | Bridewell | A61Q 19/00 |

* cited by examiner

| SAMPLE | KNOTS LEVEL (%) | DUST LEVEL | SALINE CAPACITY g/g |
|---|---|---|---|
| UNTREATED CURLY PULP | 17.5 | <5% | 16.89 |
| SAWMILL TREATED CURLY PULP | 2.25 | <5% | 17.42 |
| REGULAR HAMMERMILL TREATED CURLY PULP | 2.0 | >15% | 8.5 |

PLASTIC FREE WET WIPES WITH HIGH BULK AND WET STRENGTH

CROSS-REFERENCE TO RELATED PATENT APPLICATIONS

This patent application claims the benefit of U.S. Provisional Patent Application No. 62/994,586, filed Mar. 25, 2020, the entire teachings and disclosure of which are incorporated herein by reference thereto.

FIELD OF THE INVENTION

This invention generally relates to wet wipes.

BACKGROUND OF THE INVENTION

This invention generally relates to wet wipes such as for hygiene or cleaning applications. The disposable consumer wipes market is being faced with challenges related to the disposal and degradation of products after use. Plastics in the marine environment and in beach litter are further highlighting this issue. In the European Union, a legislative directive has been approved for the control of single use plastics. See EU Single Use Plastics Directive 2019/904 Jun. 5, 2019. In North America and other geographies, such legislation is being considered. See California Circular Economy and Plastics Pollution Reduction Act June 2019.

Consumer wipes have been specifically identified as one such material that would be regulated by such types of legislation. Most consumer wipes utilize plastic based fibers (typically polyester or polypropylene) as a component of the structure. These plastic fibers may be up to 80% of the structure in some baby wipes and surface cleaning wipes in order to produce a functionally effective wipe material.

The elimination and substitution of these fibers for natural based, non-plastic fibers creates challenges to develop successfully both the wet strength and the thickness (bulk) that the plastic fibers provide. It is possible to produce structures that are based of wood pulp and natural, non-plastic binders, such as starch, CMC & sugar based chemistries. However these products tend to, by themselves, be low in wet strength and very dense/flat such that they do not meet the functional or aesthetic needs of the product.

As such, there is a need in the art for an improved wet wipe that uses natural materials and is plastic free, but that provides sufficient bulk and wet strength.

SUMMARY OF THE INVENTION

The disclosure provides new and improved material for wet wipes with improved strength and/bulk characteristics while being plastic free as well as method of forming the material.

In an example, a wet wipe formed from a sheet formed from non-plastic materials is provided. The sheet has a weight of between 40-90 gsm. The sheet includes a blend of wood pulp fluff fiber and cellulosic staple fibers. The wood pulp fluff fiber has a weight percent of between 60-95%. The cellulosic staple fibers have an average fiber length of between 3-12 mm. The cellulosic staple fibers have a weight percent of between 40-5%. The sheet includes a plastic free binder. The sheet has an effective wet strength of at least 150 grams per linear inch in the cross-direction.

The cross-direction being perpendicular to a direction in which the sheet travels when it is being formed, e.g. along a width of a belt upon which the fibers are laid during the forming process.

In one example, the cellulosic staple fibers are formed from one or more of fine denier/decitex, shaped lyocell, or viscose.

In one example, the wet thickness of the sheet is between 0.7 mm and 1.8 mm for a 50 gsm product.

In one example, the cellulosic staple fibers have a modified cross-sectional shape.

In one example, the cellulosic staple fibers have a trilobal cross-sectional shape.

In one example, the cellulosic staple fibers have a flat cross-sectional shape.

In one example, the fibers have been compacted under pressure of between 4-8 Bar and the wet thickness has been maintained at between 0.7-1.5 mm.

In an example, a wet wipe formed from a sheet formed from non-plastic materials is provided. The sheet has a weight of between 40-90 gsm. The sheet includes a blend of wood pulp fluff fiber and cross-linked curly pulp. The wood pulp fluff fiber has a weight percent of between 60-95%. The cross-linked curly pulp have a weight percent of between 40-5%. The sheet includes a plastic free binder. The sheet has an effective wet strength of at least 150 grams per linear inch in the cross-direction.

In an example, a wet wipe formed from a sheet formed from non-plastic materials is provided. The sheet has a weight of between 40-90 gsm. The sheet includes a blend of wood pulp fluff fiber and a blend of cellulosic staple fibers and cross-linked curly pulp. The wood pulp fluff fiber has a weight percent of between 60-95%. The blend of cellulosic staple fibers and cross-linked curly pulp have a weight percent of between 40-5%. The sheet includes a plastic free binder. The sheet has an effective wet strength of at least 150 grams per linear inch in the cross-direction.

In one example, the cellulosic staple fibers of the blend of cellulosic staple fibers and cross-linked curly pulp has an average fiber length of between 3-12 mm.

In one example, the cross-linked curly pulp has been treated with a sawmill system.

In one example, the blend of cellulosic staple fibers and cross-linked curly pulp has a weight percentage of 5-40% of cellulosic staple fibers and a weight percentage of 5-40% of cross-linked curly pulp.

In one example, the cross-linked curly pulp has a knots level of less than 10% and preferably less than 5% and more preferably less than 3%.

In one example, the cross-linked curly pulp has a dust level of less than 10% and more preferably of less than 5%.

In one example, the cross-linked curly pulp has a saline capacity of at least 10 grams per gram and at least 15 grams per gram.

In one example, the forming process is airlaid.

In one example, the plastic free binder is natural.

In one example, the plastic free binder is any one or more of carboxymethyl cellulose, modified starch and/or modified sugars.

In one example, the wet thickness of the sheet is between 0.7 mm and 1.8 mm for a 50 gsm product.

In an example, a method of forming a wet wipe includes forming a sheet from non-plastic materials, the sheet having a weight of between 40-90 gsm. The step of forming includes blending wood pulp fluff fiber and cellulosic staple fibers. The wood pulp fluff fiber has a weight percent of between 60-95%. The cellulosic staple fibers have an average fiber length of between 3-12 mm. The cellulosic staple fibers has a weight percent of between 40-5%. The step of forming includes air laying the blend of wood pulp fluff fiber and cellulosic staple fibers to form a web. The step of forming includes applying a plastic free binder to the web. The sheet has an effective wet strength of at least 150 grams per linear inch in the cross-direction.

In one example, the method includes compressing the web under pressure from 4-8 Bar while the wet thickness after compression is between 0.7-1.5 mm. The step of compression occurs prior to the step of applying the plastic free binder.

In an example, a method of forming a wet wipe includes forming a sheet from non-plastic materials, the sheet having a weight of between 40-90 gsm. The step of forming includes blending wood pulp fluff fiber and cross-linked curly pulp. The wood pulp fluff fiber has a weight percent of between 60-95%. The cross-linked curly pulp has a weight percent of between 40-5%. The step of forming includes air laying the blend of wood pulp fluff fiber and cellulosic staple fibers to form a web. The step of forming includes applying a plastic free binder to the web. The sheet has an effective wet strength of at least 150 grams per linear inch in the cross-direction.

In one example, the method includes compressing the web under pressure from 4-8 Bar while the wet thickness after compression is between 0.7-1.5 mm. The step of compression occurs prior to the step of applying the plastic free binder.

In an example, a method of forming a wet wipe includes forming a sheet from non-plastic materials, the sheet having a weight of between 40-90 gsm. The step of forming includes blending wood pulp fluff fiber and a blend of cellulosic staple fibers and cross-linked curly pulp. The wood pulp fluff fiber has a weight percent of between 60-95%. The blend of cellulosic staple fibers and cross-linked curly pulp has a weight percent of between 40-5%. The step of forming includes air laying the blend of wood pulp fluff fiber and cellulosic staple fibers to form a web. The step of forming includes applying a plastic free binder to the web. The sheet has an effective wet strength of at least 150 grams per linear inch in the cross-direction.

In one example, the method includes compressing the web under pressure from 4-8 Bar while the wet thickness after compression is between 0.7-1.5 mm. The step of compression occurs prior to the step of applying the plastic free binder.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

A wet wipe formed in accordance with the application uses non-plastic materials. In one implementation, the wet wipe is an airlaid pulp based nonwoven. The wet wipe uses standard wood pulp fiber in combination with cellulosic fibers to provide high wet strength and bulk. For example, the wet wipe may have a wet strength of at least 200 grams per linear inch in the cross direction as measured by INDA/EDANA Nonwovens Standard Procedures Edition 2015, Standard Procedure: NWSP 110.R0 (15) Breaking Force and Elongation of Nonwovem Materials (Strip Method) and wet bulk of at least 0.7 mm for 50 gsm product as measured by INDA/EDANA Nonwovens Standard Procedures Edition 2015, Standard Procedure: NWSP 120.6.R0 (15) Nonwoven Thickness (EDANA Method).

In order to develop the desired wet strength and wet bulk in a finished wet wipe structure, wood pulp fluff may be combined with a number of different non-standard fiber types may be employed.

For example, low diameter (decitex or denier) fibers with an average fiber length from 3 mm to 12 mm may be employed. These fibers have the capability to form a network with a natural chemical binder and wood pulp to enhance wet strength. Examples of these fibers include lyocell in a range of between 0.8-1.5 dtex and preferably approximately 1.15 dtex fiber such as that distributed by Lenzing Aktiengesellschaft of Lenzing Austria under the TENCEL tradename and viscose in a range of between 0.5 and 1.5 dtex and preferably approximately 0.9 dtex such as that distributed by Kelheim Fibres of Kelheim Germany under the DANUFIL trademark.

Figure 1:
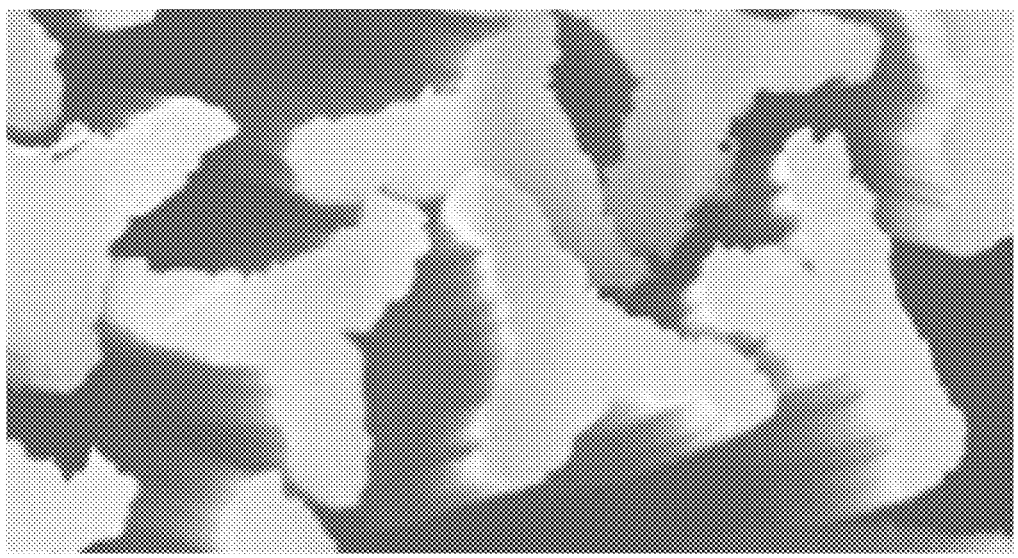
FIG. 1 illustrates a viscose fiber with a trilobal cross-section useable in examples of the present disclosure.
Figure 2:
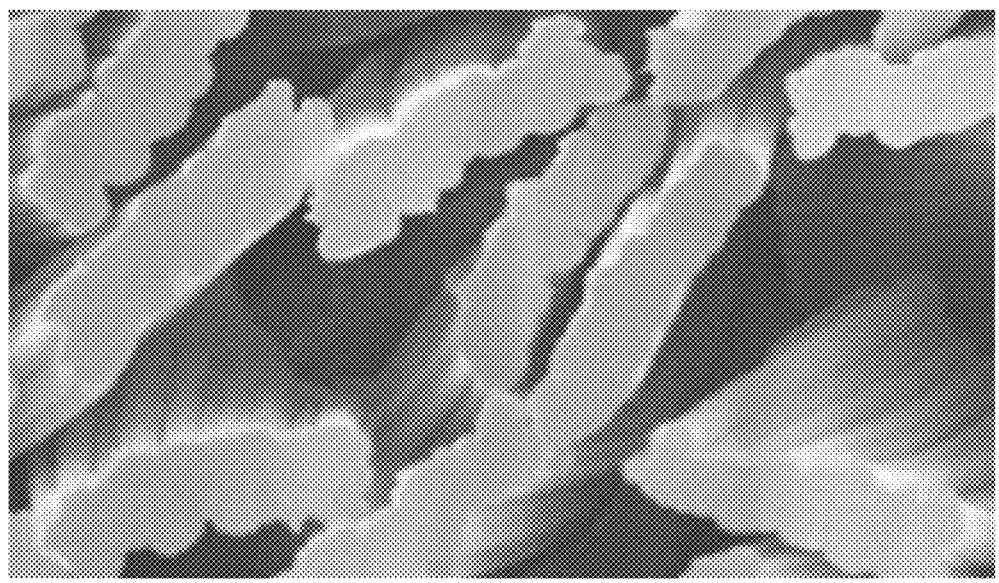
FIG. 2 illustrates a viscose fiber with a flat cross-section useable in examples of the present disclosure.
Figures 5, 6:
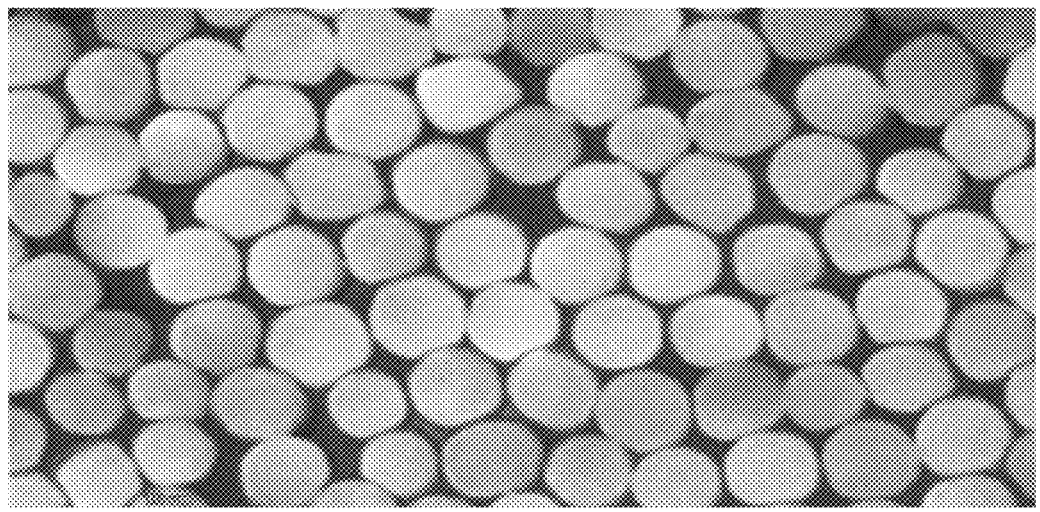
FIG. 5 illustrates a cross-section of ultrafine lyocell fibers useable in examples of the present disclosure.
FIG. 6 is a table of characteristics of cross-linked curly pulp before and after various treatments.

Other fibers that can be utilized to increase the wet bulk of the wet wipe structure are those that have a modified cross-sectional shape. FIG. 1 is a viscose fiber with a modified cross-sectional shape to having a trilobal shape distributed by Kelheim Fibres under the GALAXY tradename. FIG. 2 is a viscose fiber with a modified cross-sectional shape having a flat cross-sectional shape distributed by Kelheim Fibres under the VILOFT tradename. These modified cross-sectional shapes improve wet bulk by changing the way in which the fibers pack together and providing a modified resistance to pressure. FIG. 5 illustrates ultrafine lyocell fibers that may be incorporated. To be considered ultrafine, the lyocell fibers have a fineness of below 1.3 dtex.

Figure 3:
FIG. 3 illustrates a cross-linked curly pulp fiber useable in examples of the present disclosure.

Further, cross-linked wood pulp fiber also referred to as "cross-linked curly wood pulp fiber" or "cross-linked curly pulp" can be used to retain the wet bulk or wet strength (e.g. resiliency) of the wet wipe structure. For example, International Paper grades CMC530/CMF530/GMF530/TR195/TR195A may be incorporated. FIG. 3 illustrates representative cross-linked wood pulp fiber.

The above identified fibers may undergo opening processing to allow them to be effectively processed using airlaid equipment. For example, in the case of the cellulosic staple fibers (e.g. lyocell or viscose as discussed above) undergo a series of mechanical combing and air conveying in order to break the product into their individual fibers. This allows these cellulosic staple fibers to be admixed successfully with standard fluff wood pulp allowing the resulting blend of materials to obtain the desired functional wet strength and bulk.

Figure 4:
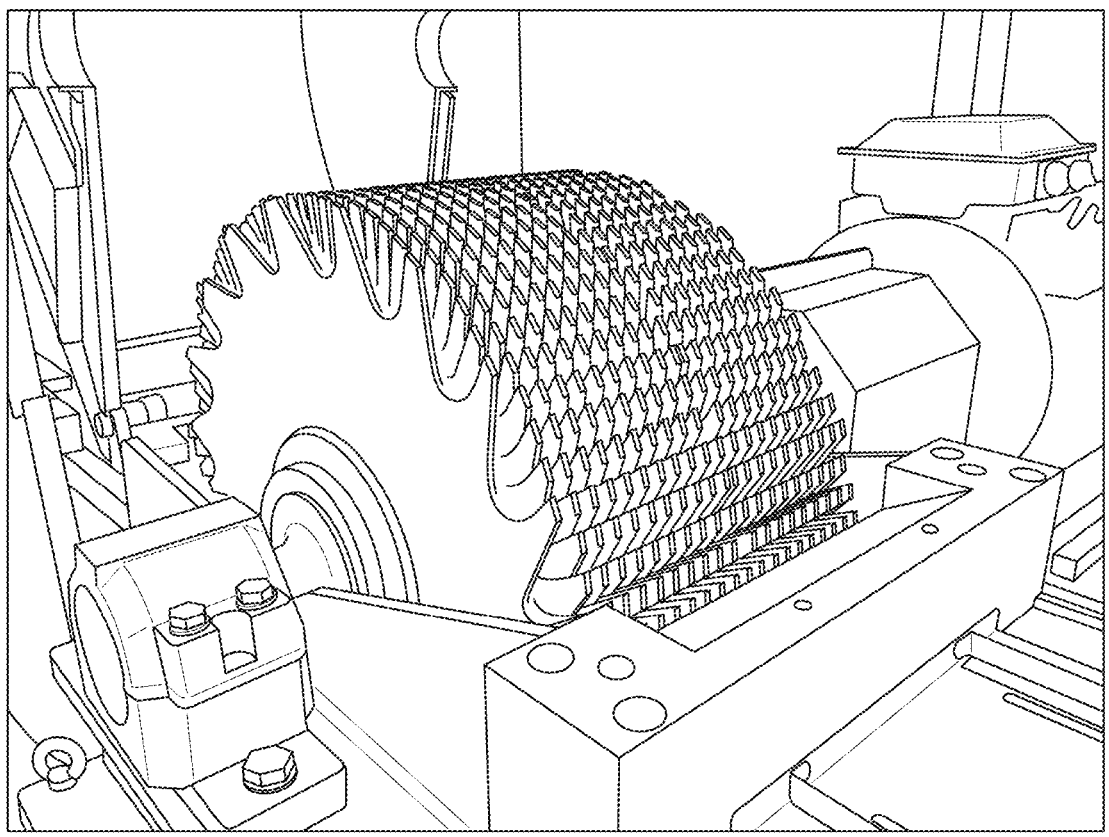
FIG. 4 illustrates a sawmill treatment system.

In the case of the cross-linked curly pulp fibers, a specific low speed sawmill treatment is required to open these fibers without breaking the fibers and creating dust and destroying their effectiveness to enhance bulk. A representative sawmill treatment system for processing the cross-linked curly pulp fibers is illustrated in FIG. 4. The sawmill process would be carried out prior to admixing with the wood pulp fluff.

Preferably, the cross-linked curly pulp fibers have a knots level of less than 10% and even more preferably less than 5% and even more preferably less than 3%. The knots level is measured by way of Scandinavian Pulp & Paper Board Testing Method SCAN 37-8. Typically knots level relates to the amount of dense clumps in the product. A clump is defined as assembly of fibers that is denser in nature than about 1-4 mm in diameter.

Preferably, the dust level of the cross-linked curly pulp fibers is less than 10% and more preferably less than 5%. The dust level is the amount of dust that the product has. Dust is defined as fibers having a fiber length of less than 0.2 mm. High levels of dust make the product difficult to process and reduces yield.

Preferably, the saline capacity of the cross-linked curly pulp fibers is at least 10 grams per gram and more preferably at least 15 grams per gram. This is measured using the International Paper test which measures the amount of saline liquid that the cross-linked curly pulp absorbs and retains under pressure. It is a measure of the products wet resilience prior to the product being admixed with the wood pulp fluff.

FIG. 6 is a chart of characteristics of cross-linked curly pulp before and after different types of treatment. More particularly, after being sawmill treated or hammermill treated. While hammer mill treatment provides decent knots levels, it has a high dust content and low saline capacity. Conversely, sawmill treatment provides good knots levels, dust levels and saline capacity.

The above identified fibers can be blended with wood pulp formed during an airlaid process. The airlaid fibers can then be compressed, such as by way of compaction rolls, to help develop strength. Typically, compaction reduces product thickness, which undesirably reduces bulk. However, the use of cellulosic staple fibers or cross-linked curly pulp mitigates the reduction in thickness while maintaining strength properties.

The desired fiber blend for achieving desired wet strength and bulk is 60% to 95% by weight wood pulp fluff and 40% to 5% by weight cellulosic staple fibers or cross-linked curly pulp. More preferably, the blend is 70-90% by weight wood pulp fluff at 70 to 90% and 30-10% by weight cellulosic staple fibers or cross-linked curly pulp.

In some implementations, the portion of the blend formed from cellulosic staple fibers or cross-linked curly pulp is a mixture of both cellulosic staple fibers and cross-linked curly pulp.

After forming the fiber blends above, the fiber blends are sprayed with a natural, plastic free chemical binder. The binder may be carboxymethyl cellulose (CMC), modified starch or modified sugars. Typically, the modified starch or modified sugars are modified with some kind of crosslinking system. These binders migrate to the crossover points of the fibers on heating and drying and form an insoluble bond during the crosslinking process.

In a preferred wet wipe, the structure of the wet wipe has a weight of 40-90 grams per square meter and preferably a wet strength of at least 150 grams per linear inch in the cross-direction. The cross-direction is defined as a direction perpendicular to the direction the product flows as it is being manufactured.

While the structure described above finds particular use in wet wipes and particularly wet wipes used as baby wipes, the structure may find additional use in feminine hygiene or diaper products (both children and adult).

Figure 7:
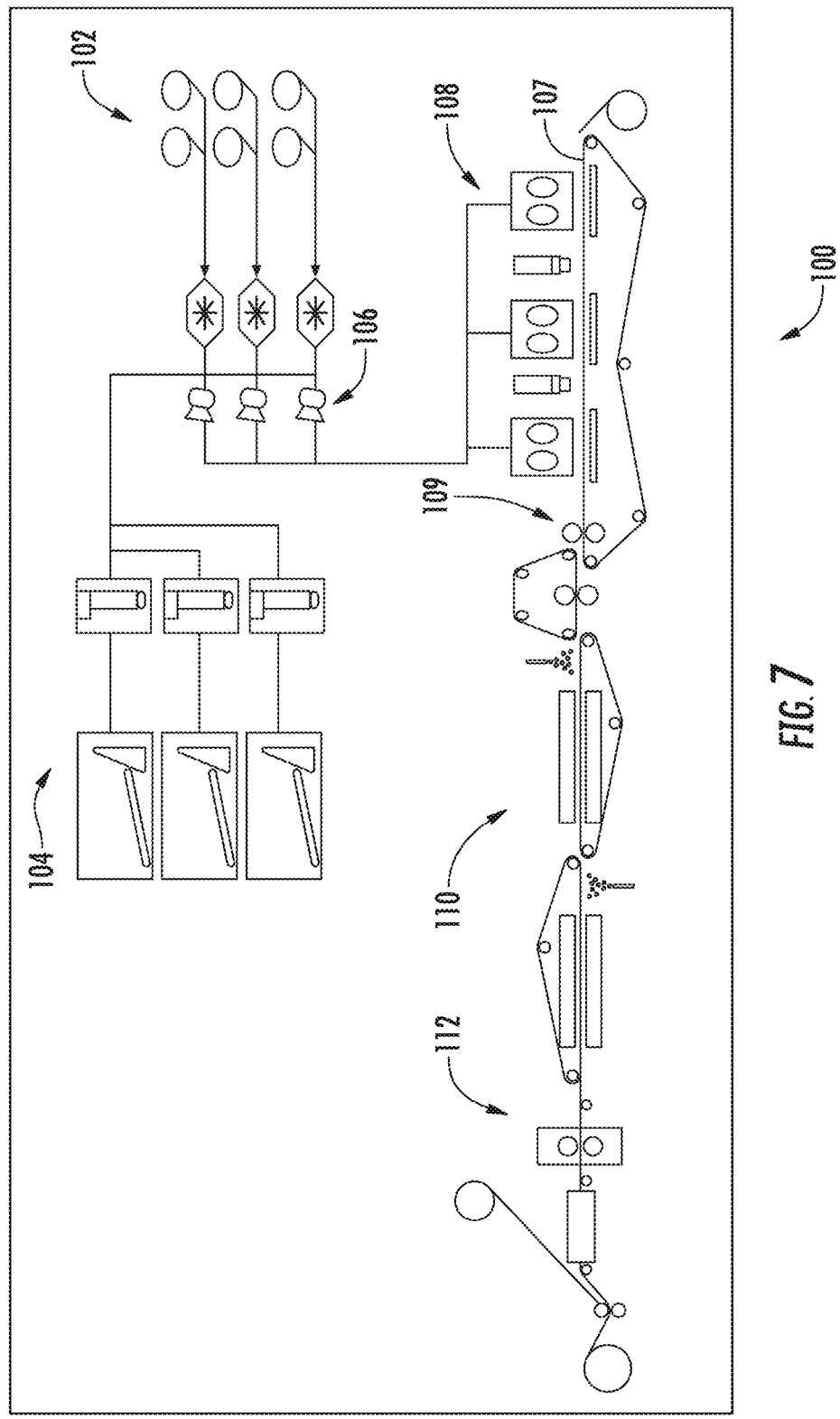
FIG. 7 is a schematic of an airlaid system for forming the material to be formed into the wet wipes of examples of the present disclosure.

FIG. 7 is a schematic illustration of a system 100 for forming the structure of the material to be formed into the sheets for wet wipes.

The system 100 includes a source of wood pulp fluff fiber 102. The wood pulp fibers may be added through the use of hammer mills.

The system 100 includes a second source of fibers 104 for supplying cellulosic staple fibers and/or cross-linked curly pulp. These fibers may be added into the system through fiber bale breakers and fiber dosing units. In some implementations, such as when cross-linked curly pulp is used, the second source of fibers 104 may include a sawmill treatment system for manipulating the cross-linked curly pulp prior to mixing with the wood pulp fluff fibers.

These wood pulp fluff fibers and the cellulosic staple fibers and/or cross-linked curly pulp fibers are transported and mixed in transport fans 106 and sent to the web forming sections 108 that include airlaid forming heads which can include forming drums.

The mixed fibers enter the forming drums from the side and vacuum is pulled at the bottom of the airlaid forming heads. The mixed fibers are distributed by perforations in the forming drums and needle rolls. The needle rolls turn in opposite directions.

As the mixed fibers are dispensed from the forming drums, the fibers are deposited on a belt 107 to form a web of the mixture of the fibers. After being deposited on the belt 107, the web and its associated fibers may be compressed by compaction rolls 109. The compression by compaction rolls 109 increases strength within the resulting material. However, the particular composition of fibers helps mitigate the typical associated reduction in bulk.

In one example, the compaction rolls 109 compact the web of the mixture of fibers under pressure of between 4-8 Bar and the wet thickness has been maintained at between 07-1.5 mm.

A web bonding region 110 can provide chemical and thermal bonding as well as apply the plastic free binder.

Thereafter, the web may be exposed to finishing processes and then removed from the belt and wound into a roll. When forming sheets for wet wipes, the web may be directly supplied to a cutting arrangement or the roll of web may be shipped to another location for forming the wet wipe sheets.

In one example, it was determined that the use of 1.15 denier lyocell fibers at mix levels of 10% and 20% enhanced both wet strength and wet thickness of wet wipe products. The following chart provides experimental data related to testing:

|  | Wet Thickness | % Increase | MD Wet | % Increase | CD Wet | % Increase |
| --- | --- | --- | --- | --- | --- | --- |
| Pulp Only | 0.85 |  | 293 |  | 236 |  |
| 10% lyocell | 1.05 | 23 | 353 | 20 | 254 | 8 |
| 20% lyocell | 0.95 | 12 | 429 | 46 | 332 | 41 |

In one example, it was illustrated that by using lyocell, such as 20% lyocell, the amount of compression could be increased to 6 Bar while maintaining or even increasing the resulting wet thickness value as compared to pulp only. Using Lycoell, also resulted in increased strength in both the machine and cross-directions due, in part, to the ability to increase the pressure. The following chart illustrates the effect on wet thickness, machine direction and cross-direction strength with increased pressure as well with increased pressure and the use of lyocell:

|  | Wet Thickness | % Increase | MD Wet | % Increase | CD Wet | % Increase |
| --- | --- | --- | --- | --- | --- | --- |
| Pulp Only 4 Bar Pressure | 0.85 |  | 293 |  | 236 |  |
| Pulp Only 6 Bar Pressure | 0.72 | −15 | 306 | 4 | 299 | 27 |
| 20% lyocell 6 Bar Pressure | 0.88 | 22 | 482 | 57 | 389 | 30 |

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A sheet for a wet wipe comprising:
    the sheet formed from non-plastic materials, the sheet having a weight of between 40-90 gsm, said sheet comprising:
    a blend of wood pulp fluff fiber with a second component, the wood pulp fluff fiber having a weight percent of between 60-95%;
    the second component having a weight percent of between 40-5%, the second component being selected from the group consisting of:
      A) a cross-linked curly pulp;
      B) cellulosic staple fibers; and
      C) a blend of a blend of cellulosic staple fibers and cross-linked curly pulp;
    a plastic free binder;
    wherein the sheet has an effective wet strength of at least 150 grams per linear inch in the cross direction and the wet thickness has been maintained at between 0.7-1.8 mm.

2. The sheet of claim 1, wherein the second component includes cellulosic staple fibers formed from one or more of lyocell between 0.8-1.5 mm, viscose between 0.5 and 1.5 dtex, shaped lyocell, or viscose.

3. The sheet of claim 1, wherein the wet thickness of the sheet is between 0.7 mm and 1.5 mm for a 50 gsm product.

4. The sheet of claim 1, wherein the second component includes cellulosic staple fibers that have a modified cross-sectional shape.

5. The sheet of claim 1, wherein the second component includes cellulosic staple fibers that have a trilobal cross-sectional shape.

6. The sheet of claim 1, wherein the second component includes cellulosic staple fibers have a flat cross-sectional shape.

7. The sheet of claim 1, wherein the blend of wood pulp fluff fiber and second component has been compacted under pressure of between 4-8 Bar and the wet thickness has been maintained at between 0.7-1.5 mm.

8. The sheet of claim 1, wherein the second component includes cellulosic staple fibers, the cellulosic staple fibers have an average fiber length of between 3-12 mm.

9. The sheet of claim 1, wherein the second component includes cross-linked curly pulp that has been treated with a sawmill system.

10. The sheet of claim 1, wherein the second component includes a blend of cellulosic staple fibers and cross-linked curly pulp that has a weight percentage of 5-40% of cellulosic staple fibers and a weight percentage of 5-40% of cross-linked curly pulp.

11. The sheet of claim 1, wherein the second component includes cross-linked curly pulp that has a knots level of less than 10%.

12. The sheet of claim 11, wherein the second component includes cross-linked curly pulp that has a knots level of less than 5%.

13. The sheet of claim 11, wherein the second component includes cross-linked curly pulp that has a knots level of less than 3%.

14. The sheet of claim 1, wherein the second component includes a cross-linked curly pulp that has a dust level of less than 10%.

15. The sheet of claim 14, wherein the second component includes a cross-linked curly pulp that has a dust level of less than 5%.

16. The sheet of claim 1, wherein the second component includes a cross-linked curly pulp having a saline capacity of at least 10 grams per gram.

17. The sheet of claim 16, wherein the second component includes a cross-linked curly pulp having a saline capacity of at least 10 grams per gram.

18. The sheet of claim 1, wherein the forming process is airlaid.

19. The sheet of claim 1, wherein the plastic free binder is natural.

20. The sheet of claim 1, wherein the plastic free binder is any one or more of carboxymethyl cellulose, modified starch and/or modified sugars.

21. A sheet for a wet wipe comprising:
the sheet formed from non-plastic materials, the sheet having a weight of between 40-90 gsm, said sheet comprising:
a blend of wood pulp fluff fiber and a blend of cellulosic staple fibers and cross-linked curly pulp, the wood pulp fluff fiber having a weight percent of between 60-95%, the blend of cellulosic staple fibers and cross-linked curly pulp having a weight percent of between 40-5%;
a plastic free binder;
wherein the sheet has an effective wet strength of at least 150 grams per linear inch in the cross-direction and the wet thickness has been maintained at between 0.7-1.8 mm.

22. A method of forming a sheet for a wet wipe comprising:
forming the sheet of claim 1 from non-plastic materials, the sheet having a weight of between 40-90 gsm, said forming comprising:
blending wood pulp fluff fiber with a second component, the wood pulp fluff fiber having a weight percent of between 60-95% and the second component having a weight percent of between 40-5%, the second component being selected from the group consisting of:
A) a cross-linked curly pulp;
B) cellulosic staple fibers; and
C) a blend of a blend of cellulosic staple fibers and cross-linked curly pulp;
air laying the blend of wood pulp fluff fiber and cellulosic staple fibers to form a web;
applying a plastic free binder to the web; and
wherein the sheet has an effective wet strength of at least 150 grams per linear inch in the cross-direction and the wet thickness has been maintained at between 0.7-1.8 mm.

23. The method of claim 22 further comprising, compressing the web under pressure from 4-8 Bar while the wet thickness after compression is between 0.7-1.5 mm.

24. A method of forming a sheet for a wet wipe comprising:
forming a sheet from non-plastic materials, the sheet having a weight of between 40-90 gsm, said forming comprising:
blending wood pulp fluff fiber and cross-linked curly pulp, the wood pulp fluff fiber having a weight percent of between 60-95%, the cross-linked curly pulp having a weight percent of between 40-5%;
air laying the blend of wood pulp fluff fiber and cross-linked curly pulp to form a web;
applying a plastic free binder to the web; and
wherein the sheet has an effective wet strength of at least 150 grams per linear inch in the cross-direction and the wet thickness has been maintained at between 0.7-1.8 mm.

25. A method of forming a sheet for a wet wipe comprising:
forming a sheet from non-plastic materials, the sheet having a weight of between 40-90 gsm, said forming comprising:
blending wood pulp fluff fiber with a blend of cellulosic staple fibers and cross-linked curly pulp, the wood pulp fluff fiber having a weight percent of between 60-95%, the blend of cellulosic staple fibers and cross-linked curly pulp having a weight percent of between 40-5%;
air laying the blend of wood pulp fluff fiber and blend of cellulosic staple fibers and cross-linked curly pulp to form a web;
applying a plastic free binder to the web; and
wherein the sheet has an effective wet strength of at least 150 grams per linear inch in the cross-direction and the wet thickness has been maintained at between 0.7-1.8 mm.

26. A sheet for a wet wipe comprising:
the sheet formed from non-plastic materials, the sheet having a weight of between 40-90 gsm, said sheet comprising:
a blend of wood pulp fluff fiber and cross-linked curly pulp, the wood pulp fluff fiber having a weight percent of between 60-95%, the cross-linked curly pulp having a weight percent of between 40-5%;
a plastic free binder;
wherein the sheet has an effective wet strength of at least 150 grams per linear inch in the cross-direction and the wet thickness has been maintained at between 0.7-1.8 mm.

* * * * *